United States Patent [19]

Groman et al.

[11] 4,288,538

[45] Sep. 8, 1981

[54] TEST METHOD AND COMPOSITION THEREFOR

[75] Inventors: Ernest V. Groman, Sommerville; Marian E. Sacco, Rochester, both of N.Y.

[73] Assignee: Baxter Travenol Laboratories, Inc., Deerfield, Ill.

[21] Appl. No.: 8,124

[22] Filed: Jan. 31, 1979

[51] Int. Cl.$^3$ ...................... C12Q 1/134; C01N 31/14
[52] U.S. Cl. .......................................... 435/7; 435/18; 435/52; 435/262; 435/280; 424/1.5; 424/12; 23/230 B
[58] Field of Search .................. 23/230 B; 424/1, 1.5, 424/12; 435/7, 18, 52, 280, 262, 810

[56] References Cited

U.S. PATENT DOCUMENTS

| | | | |
|---|---|---|---|
| 3,094,465 | 6/1963 | Nishikawa et al. | 435/52 |
| 3,646,396 | 2/1972 | Catt | 435/7 |
| 4,062,733 | 12/1977 | Edwards | 435/7 |
| 4,166,104 | 8/1979 | Wagner et al. | 424/12 |

FOREIGN PATENT DOCUMENTS 2618511 11/1976 Fed. Rep. of Germany .

OTHER PUBLICATIONS

Katagiri, et al., "Estriol In Pregnancy III Developement, Comparison and Use of Specific Antisera for Rapid Radio Immunoassay of Unconjugated Estriol in Pregnancy Plasma", *Steriods*, vol. 24, No. 2, (1974), pp. 225-238.
Albrecht, et al., "Rapid Enzyme Hydrolysis of Urine Extracts for Estriol Analysis", *Steroids*, vol. 25. No. 5, (1975), pp. 587-590.
Levitz et al., "16-Sutfates of Estriol in Body Fluids of Human Pregnancy at Term", *Steroids*, vol. 27, No. 2, (1976), pp. 287-294.
Jeffcoate "The Use of $^{125}$Iodine Tracers in Steriod Radio Immunoassays", *R.I.A. of Steroid Hormones*, Gupta ed. Verling Chemie Ginblt., Weinheim, (1975), pp. 185-195.
Tulchinsky, "The Value of Estrogens in the High-Risk Pregnancy", *Management of the High-Risk Pregnancy, ed. W. N. Spellacy, University Park Press, Baltimore, (1975), pp. 29-47*.
Total Estriol RIA Kit Code 1M 82", Amersham Corp., Arlington Heights, ILL., (Jun. 1978).

*Primary Examiner*—Thomas G. Wiseman
*Attorney, Agent, or Firm*—Paul C. Flattery; Lawrence W. Flynn; Max D. Hensley

[57] ABSTRACT

Test methods in which an enzyme conversion of at least one member of a family of compounds to an analyte precedes an immunoassay of the analyte are improved by conducting the enzyme conversion step substantially simultaneous with the immunoassay. A novel composition is provided for conducting the improved test method.

40 Claims, No Drawings

TEST METHOD AND COMPOSITION THEREFOR

BACKGROUND OF THE INVENTION

Many analytical methods are directed towards the determination of a family of closely related compounds. These families of compounds may arise in a test sample by a variety of mechanisms. For example, manufacturing operations often yield in addition to the desired product, a number of analogues, homologues or other derivatives. Further, families of compounds may be produced by the metabolic activity of living organisms on substances introduced into or produced within the organism.

It is frequently desired to determine all of the members of a family of compounds. For example, if the family members have similar biological activity it would be clinically useful to determine the concentration of the entire family. Similarly, a single compound may be clinically significant but available test samples may not contain a representative quantity of the compound because it has already been metabolically converted into other substances. Further, since precursors may be readily converted into the substance of interest in vivo it may be clinically useful to assay the precursors as well as the substance of interest. Thus from the standpoint of biological activity it may be most instructive to assay an entire family of metabolic relatives of the target compound. This is particularly the case with drugs and naturally occurring steroids which are commonly subject to hydrolysis, condensations and redox conversions as part of the normally occurring metabolism of the body. Estriol assays are an example.

Estriol, an estrogen produced by the placenta, is assayed to monitor fetal viability. As a practical matter the estriol must be measured in the mother's plasma or urine. However, the mother's liver anabolizes estriol to various sulfate and glucuronide conjugates; only a small proportion of estriol is found in the plasma or urine. Thus, an adequate measure of placental estriol elaboration must include a reconversion of the estriol anabolic conjugates to estriol. While it is possible to determine the amount of each conjugate in the estriol family, it is more convenient to simply convert the conjugates into estriol. Then a single assay will measure the total amount of estriol produced by the placenta.

Receptor binding assays are frequently used to determine families of compounds. Receptor binding assays all exploit the capacity of a receptor, usually a protein such as an antibody, to recognize and reversibly bind an analyte. For example, in the commonly encountered competitive immunoassay technique, a receptor antibody is equilibrated with the analyte and a labeled analogue of the analyte. The labeled analogue usually contains a covalently bound moiety, e.g., a radioisotope or enzyme, which is foreign to the other constituents of the assay. The labeled analogue, however, is labeled so that it is recognized and bound by the receptor with approximately the same affinity as the analyte. A deficiency of receptor binding sites compared to the total of labeled plus sample analyte binding sites is provided, thus forcing the labeled and sample analytes to compete for a limited number of receptor sites. Since the labeled and sample ligand have an approximately equivalent affinity for the receptor, the total amount of labeled analyte bound to the receptor will be inversely proportional to the amount of sample analyte. The receptor-bound analyte, both labeled and unlabeled, can then be separated from the remaining unbound analyte and the quantity of receptor-bound label compared with a standard curve to arrive at a quantitative measure of the sample analyte.

A principal difficulty in assaying a family of compounds by a receptor binding method is that it is not practical to prepare a receptor which indiscriminately binds all members of a family of compounds with the same affinity. While an antibody raised by known techniques against a first member of the family may indeed bind, i.e., cross-react with other members of the family, the antibody will rarely exhibit the same affinity for each member. The result is that some members will be preferentially bound at equilibrium over others. This will seriously distort the results of any assay using such a receptor. For example, it would be impossible to determine from a single receptor assay whether an elevated total for the family was a function of either a predominant proportion of high affinity analyte or higher concentration of low affinity analyte. Of course, a combined assay for a family of compounds is clearly impossible where the receptor fails to cross-react at all with some of the family members. One must then go to the expense and difficulty of conducting a plurality of determinations. Accordingly the nature of the receptors used in receptor binding assays makes it particularly desirable to convert all of the family members either to one of the family members or to a single compound not one of the family members.

Such a conversion has been incorporated by the prior art into a method for the determination of estriol. Free estriol and the estriol conjugates estriol-16-glucuronide, estriol-3-sulfate-16-glucuronide, estriol-3-sulfate and estriol-3-glucuronide are a family of estriol and its anabolites that are of clinical interest. The prior art method for the determination of this family comprises incubating the test sample with enzymes capable of hydrolyzing the glucuronide and sulfate conjugates to estriol. When the conversion to estriol is complete, the amount of estriol in the hydrolyzed sample is then determined by competitive radioimmunoassay. See, for example, Levitz et al and Horecht et al in "Steroids" at 27:287-294 (1976) and 25:587-590 (1975), respectively.

In all of the prior art methods for estriol and its conjugates of which applicants are aware the enzyme hydrolysis has been allowed to go to completion before the radioimmunoassay is conducted. The reasons for this are believed to be a concern that the enzyme incubation and the radioimmunoassay will mutually interfere.

First, the pH commonly employed for enzyme hydrolysis of estriol glucuronides and sulfates is about from 4 to 6, generally about 5. However, the pH at which antibody binding of haptens is ordinarily considered optimal is about from pH 7 to 8. Further, the enzyme preparations may contain proteases; these clearly could be deleterious to antibodies, particularly if the antibodies were exposed to the proteases throughout the enzyme incubation period.

Second, it is known that estriol antibodies cross-react with such estriol conjugates as estriol-3-sulfate and estriol-3-glucuronide. See Katagiri et al, "Steroids" 24:225-239 (1974). Yet these same conjugates must be enzyme hydrolyzed to estriol if the assay is to be accurate. Since the estriol antibody binds to these estriol conjugates it could be expected that the antibody would sterically hinder access of the enzyme to the conjugate. This could of course prevent the hydrolysis of the estriol conjugates entirely or, at the least, could excessively extend the period for their hydrolysis. In this connection, see U.S. Pat. Nos. 3,852,157 and 3,935,074, W. German Offenlegungsschrift 2,618,511 and French Patent Number 2,373,063.

This prior art procedure, however, is disadvantageous in several ways. First, the enzyme composition in commercial estriol assay kits must be separately packaged from the estriol antibody. This, of course, increases the cost of the kits. Second, the conduct of the prior art assay is complicated by the need to separately add the enzyme composition and to time the enzyme incubation period. This introduces additional sources of error into the assay. Third, the time for performing the assay is extended by the period of the enzyme incubation or the radioimmunoassay, whichever is shorter. This extended period of at least one hour is a serious impediment to the prompt conclusion of the determination.

OBJECTS OF THE INVENTION

Accordingly it is an object of this invention to reduce the time previously required to conduct receptor binding assays of an enzyme-pretreated sample.

It is an additional object to reduce the cost of packaging the components used in the performance of such assays.

These and other objects of this invention will be apparent to those skilled in the art from a consideration of this specification taken in its entirety.

SUMMARY OF THE INVENTION

It has surprisingly been found that in receptor binding assays for the total amount of a family of compounds in a test sample wherein the test sample is contacted first with an enzyme composition to convert the family of compounds into an analyte and then with a receptor for the analyte, the above objects are attained by contacting the sample with the receptor before the enzyme composition has completed converting the family of compounds into the analyte. It was most unexpected that the enzyme conversion and antibody binding can be accomplished together within 30 minutes, even though antibody is present, whereas these steps have heretofore been reported as requiring more than 3 hours when practiced sequentially.

A novel reagent is provided for the combined assay of this invention, comprising a receptor for an analyte and an enzyme composition for converting a family of compounds into the analyte, the reagent being essentially free of the analyte.

Since the enzyme hydrolysis is not complete, and may not even have started when the receptor is added in accordance with this invention, a novel material is produced during the practice of the improved assay described herein. This material comprises an enzyme composition, a substrate for the enzyme composition and a receptor for a product of the enzyme composition acting upon the substrate.

DESCRIPTION OF THE PREFERRED EMBODIMENTS

The families of compounds which can be determined in accordance with this invention include all groups of substances which may be enzymatically converted to a single analyte suitable for assay by a receptor binding method. Ordinarily the families of compounds will be those which can be converted to a single analyte by enzymatic isomerization, hydrolysis, or reduction or oxidation of the family members. In general, the composition of the family will depend upon such factors as the sample selected for assay and the biological activity of the family members. Thus the selection largely will be a function of the practical limits imposed by the test sample composition and the clinical interest which the family holds for the artisan. The family members need not be closely related structurally or functionally, although it is often that families of compounds having a common diagnostic interest will be so related. The families are not necessarily composed of discrete compounds but may include absorbed complexes, metal chelates and the like. Likewise, the families need not be composed entirely of water soluble substances. For example, it may be desirable to assay the total of an analyte free in solution in the sample and analyte which is reversibly bound by an absorbant such as a soluble or insoluble protein. Enzymatic digestion of the absorbant will release the analyte into solution for analysis. Families of compounds which may be enzymatically converted to aldosterone, cortisol, testosterone, diethylstilbestrol, terbutaline and estriol may all be determined according to the method herein. An exemplary family in the case of estriol is described above.

It is most convenient to select one member of a family of compounds into which the other members may be converted. This member may be the predominant member to be found in the test sample, the member for which the most sensitive assay can be prepared, or the member having the most significant biological activity. The most rapid enzyme conversion can ordinarily be accomplished by employing the minor family members as substrates for enzymes capable of yielding the predominant family member since less substrate will need to be converted. However, the decision regarding which analyte to use will also rest upon the enzyme kinetics and cost. For example, a proportionately minor component of the family may be selected if the enzyme kinetics capable of converting the other family members into the minor component are sufficiently rapid and favor the desired direction, or if the enzyme is available at low cost so that high enzyme activities can be employed.

Alternatively, the entire family of compounds can be converted into an analyte which is not one of the original family. Selection of this alternative will be based upon the same considerations as for selecting a given family member as analyte. In general, however, converting all of the family members to a foreign analyte will be less efficient than converting the minority proportion of family members to one of the family members. Accordingly, this alternative ordinarily is not preferred.

A wide variety of enzymes may be employed in the practice of this invention. While the enzymes should not exhibit significant activity which is deleterious to the receptor chosen for use in the assay, as a practical matter enzymes are highly specific for given substrates and may be readily selected to be substantially inert towards catalytic degradation of the receptor. The enzymes selected will depend upon the family members to be determined and the desired analyte. Exemplary enzymes which may be used are transferases, decarboxylases, hydrolases, isomerases, hydrolytic enzymes such as esterases and carbohydrases and oxidation-reduction enzymes such as dehydrogenases and oxidases. In this assay of the estriol family of compounds described above the desired enzymes are glucuronidase and sulfatase. They are readily available from commercial sources or may be prepared by known methods.

Proteases may also be used if a receptor is supplied which is not susceptible to proteolytic hydrolysis. For example, the $Fab_2$ fragment of immunoglobulin G is capable of reversibly binding haptens or antigens but is not susceptible to papain hydrolysis. Thus papain may be used as the protease with such a receptor. Alternatively, since many proteolytic enzymes cleave proteins only at certain amino acid residues, the residues may be covalently modified so as to block the action of the enzyme. However, since the test sample protein is not so modified it is possible to simultaneously hydrolyze the sample without adversely affecting the receptor.

The receptor may be any substance which is capable of reversibly binding the analyte. The great preponderance of suitable receptors are proteins such as antibodies, cell surface receptors and specific binding proteins such as thyroxine binding globulin or intrinsic factor. Suitable receptors and techniques for their use are well known in the immunoassay art and may be readily adapted for use herein. The receptor is preferably an antibody raised against the analyte. Such receptors may be prepared in accordance with conventional procedures. It is not necessary to purify the antibody or even to separate the plasma fraction containing antibodies; the raw plasma may be used satisfactorily.

The central feature of this invention is the combination of receptor binding of analyte while at the same time conducting the enzyme conversion of the family of compounds to the analyte. Since the prior art teaches contacting the sample with the receptor only after the enzyme conversion is complete, it is within the scope of this invention to add the receptor to the enzyme and sample mixture at any point up until the completion of the enzyme conversion. However, two of the advantages of this invention, i.e., the elimination of separate packaging for enzyme and receptor and the elimination of error introduced by timing and adding the receptor as a separate step, are foreclosed unless the receptor and enzyme are added to the sample together. Further, the total assay time is gradually prolonged the later the receptor is contacted with the mixture of enzyme and sample. Thus it is preferred that the receptor and the enzyme composition be contacted with the sample at least substantially simultaneously. It is most preferred that the receptor and enzyme composition be premixed and then added to the sample.

This premixed reagent includes the receptor for an analyte and an enzyme composition for converting the family of compounds to the analyte. While the reagent should be essentially free of analyte, since this will clearly interfere in the assay, any other substances which will not adversely affect either substrate conversion by enzyme or the receptor binding of analyte may be included in the reagent. For example, buffers, dyes, protein stabilizing substances such as carbohydrates, salts, saccharides or inert proteins, and antimicrobial substances such as sodium azide may be included in the reagent. The reagent is preferably an aqueous solution. However, this solution may be lyophilized to improve its shelf life.

Certain receptor binding assays use a water soluble receptor to bind analyte and tracer, followed by the removal of the receptor from solution. Ordinarily the receptor is removed from solution through immune-precipitation by an antibody capable of binding the analyte receptor. However, this precipitation step may be eliminated if the receptor is insolubilized before the assay. Many suitable techniques for doing so are well known, e.g., U.S. Pat. No. 3,646,346, and may be readily employed in the practice of this invention. For example, receptors may be cross-linked to render them insoluble, they may be covalently bonded to or absorbed onto solid particles or the inner walls of the assay reaction container or they may be cross-linked and then so absorbed. Where the receptor is absorbed onto or cross-linked to the walls of a container, the enzyme composition may be conveniently placed in the container either dry or as an aqueous solution. Handling of the containers prior to the assay is somewhat more convenient if the composition is dry. Hence the term reagent is applied to the novel reagent herein encompasses dry or liquid compositions, portions of which may be integral with or absorbed to a formed object such as a container.

The reagent may also contain a tracer for the analyte. Such tracers are well known in the art. They are generally analyte analogues having a detectable group covalently linked directly or by way of a binding group to a region of the analyte that is not expected to be bound by the analyte receptor. The detectable group is preferably a radioisotope such as $^{131}I$ or $^{125}I$, although enzymes, stable free radicals or coenzymes are also suitable. Methods for making tracers are conventional, and many tracers are commercially available. For example, suitable radioiodinated estriol tracers may be prepared following the procedure disclosed by Nars et al, "J. Endocrin." 57:xlvii (1973).

The reagent of this invention is used in known receptor binding assays in the same way that receptors are normally used in such assays. Hence the reagent may be used with any of the competitive, sandwich or junction, sequential saturation, or homogeneous receptor binding methods. These methods are all conventional and well known in the art. Estriol has heretofore been determined by a competitive method as described above and, in addition, the competitive binding method is reviewed in Zettner, "Clinical Chemistry" 19 (7):699–705 (1973). Examples of homogenous methods, i.e., those which do not require a phase separation, are disclosed in U.S. Pat. Nos. 3,935,074 and 3,852,157. The sequential saturation technique is reviewed by Zettner et al in "Clinical Chemistry" 20(1):5–14 (1974). The sandwich method, among others, is described in Kirkham et al, *Radioimmunoassay Methods* (1971).

In a representative competitive immunoassay for a family of compounds to be determined in accordance with this invention, an aliquot of the test sample is mixed with an enzyme composition for converting the family of compounds into one member of the family which will function as an analyte for the assay, serum containing an antibody capable of binding the analyte, and a radioisotopically labeled analogue of the analyte under conditions suitable for converting the compounds and for binding the analyte. The amounts of enzyme, receptor and tracer are the same as used in the known competitive method in which the enzyme treatment precedes the immunoassay. Ordinarily the amount of enzyme will be sufficient to substantially completely convert the family members to analyte within about three hours. This reaction mixture is then incubated for from about 15 minutes to three hours at from about 4° C. to 37° C., with 30 minutes at 37° C. being preferred. Then antiserum raised against the receptor-containing serum is added to precipitate the receptor with its bound analyte and tracer. It is desirable to also add a precipitation aid such as polyethylene glycol at this point. The precipitated receptor is removed from suspension by centrifugation of the reaction container at 1000×g for 15 minutes, the residual solution is decanted and the containers counted for radioactivity. Standards are prepared in the same fashion. A comparison of the sample counts with the standards will then disclose the amount of the family of compounds in the test sample.

The following examples are intended to further illustrate the invention, although it will be understood that the invention is not limited to these specific examples.

EXAMPLE I

This example discloses the preparation of a reagent for immunoassay of estriol and its glucuronide and sulfate conjugates. Estriol antiserum is prepared by immunizing rabbits against estriol-6-(0-carboxymethyl) oxime linked to bovine serum albumin in accordance with Katagiri et al supra. 3 liters of 0.1 M maleate buffer at pH 5.2 and containing ethylenediamine tetraacetate, neomycin sulfate and bromophenol blue at about 5° C. are then slowly mixed with 175 mls of normal rabbit serum, 0.5 ml of the estriol antiserum and 500 mls of a commercially available extract of *Helix pomatia* containing β-glucuronidase (5.2 units/ml phenolphthalein glucuronide) and aryl sulfatase (2.6 units/ml phenolphthalein disulfate). The reagent is then brought to 5 liters total volume with the maleate buffer and stored at about 4° C.

EXAMPLE 2

This example demonstrates the rapidity with which an assay of estriol and its conjugates can be accomplished using the method of this invention.

$^{125}$I estriol was prepared by the method of Nars et al supra, except for the substitution of estriol-6-(0-carboxymethyl) oxime for estradiol as the starting material. The tracer solution exhibited an activity of about 0.5 μCi estriol $^{125}$I/ml.

A set of test tubes were marked in duplicate according to the schedule described below in Table 1. The following reagents are allowed to reach ambient temperature and added to the appropriate tubes in duplicate:

(a) 10 microliters of blank, standard, control or sample.
(b) 100 microliters of $^{125}$I estriol solution described above.
(c) 100 microliters of the enzyme receptor solution of Example 1.

The contents of each tube are mixed by vortexing and then incubated at 37° C. for 30 minutes. The antibody-bound estriol and $^{125}$I estriol is precipitated by the addition of 1 ml of 5% sheep antirabbit serum in phosphate buffered saline containing 6% polyethylene glycol of about 5000 average molecular weight. The suspension is centrifuged for 15 minutes at 1000 ×g and the supernatant carefully decanted. The contents of all tubes are counted for one minute with the counter window adjusted for iodine-125. The results are set forth in Table 1. The counts per minute were then plotted on semilogarithmic graph paper and the total concentration of estriol and estriol conjugates in the patient and control samples determined by interpolation.

TABLE 1

| Tube No. | Contents of Tubes | Counts per Minute (bound) | Estriol Concentration (ng/ml) |
|---|---|---|---|
| 1,2 | Estriol Serum Blank, 0 ng/ml | 41,253; 40,401 | 0 |
| 3,4 | Estriol Serum Standard, 30 ng/ml | 31,175; 31,360 | 30 |
| 5,6 | Estriol Serum Standard, 60 ng/ml | 26,013; 25,925 | 60 |
| 7,8 | Estriol Serum Standard, 100 ng/ml | 23,106; 21,863 | 100 |
| 9,10 | Estriol Serum Standard, 200 ng/ml | 18,882; 18,987 | 200 |
| 11,12 | Estriol Serum Standard, 400 ng/ml | 14,676; 15,405 | 400 |
| 13,14 | Estriol Serum Control I | 27,622; 27,508 | 48 |
| 15,16 | Estriol Serum Control II | 16,627; 16,145 | 285 |
| 17,18 | Urine Control I* | 26,346; 26,007 | 58 |
| 19,20 | Urine Control II | 22,867; 21,440 | 109 |
| 21,22 | Patient #2 Serum Sample | 16,754; 16,761 | 273 |
| 23,24 | Patient #4 Serum Sample | 15,999; 16,212 | 296 |
| 25,26 | Patient #7 Serum Sample | 20,319; 20,168 | 150 |

*Urine samples and controls are diluted 1:100 in water before the aliquot is taken The above examples and other specific information contained herein are for purposes of illustration only, and such alterations and modifications thereof as would be apparent to those skilled in the art are deemed to fall within the scope and spirit of the invention, bearing in mind that the invention is defined only by the claims appended hereto.

What is claimed is:

1. In a specific binding assay for the determination of the total amount of steriod present in a test sample containing steriod and steriod conjugates, wherein the improvement comprises, contacting the test sample substantially simultaneously with receptor for the steriod, and with an enzyme composition suitable for converting the steriod conjugates to the steriod under conditions suitable for the conversion of the steriod and the binding of steriod by the receptor.

2. The method of claim 1 wherein the receptor is an antibody.

3. The method of claim 1 wherein the enzyme is capable of hydrolytic or oxidation reduction activity.

4. The method of claim 1 wherein the enzyme composition is capable of producing estriol.

5. The method of claim 1 wherein the enzyme composition is capable of producing aldosterone.

6. The method of claim 1 wherein the enzyme composition is capable of producing cortisol.

7. The method of claim 1 wherein the enzyme composition is capable of producing testosterone.

8. The method of claim 1 wherein the enzyme composition is capable of producing diethylstilbesterol.

9. The method of claim 1 wherein the enzyme composition is capable of producing terbutaline.

10. The method of claim 1 where the enzyme composition contains a transferase, decarboxylase, hydrolase, isomerase, esterase, dehydrogenase or oxidase.

11. In a radioimmunoassay for the determination of total estriol in a test sample containing free estriol and estriol conjugates, wherein the improvement comprises, contacting the test sample substantially simultaneously with a receptor for estriol and with an enzyme composition suitable for converting the estriol conjugates at a pH from about 4 to about 6 and under conditions suitable for the conversion of the estriol conjugates and the binding of estriol by the receptor.

12. The method of claim 11 wherein a radioactive tracer is added to the test sample substantially simultaneously with the contact of the test sample with estriol receptor and conversion of the conjugates.

13. The method of claim 12 wherein the estriol receptor is insolubilized before it is contacted with the test sample.

14. The method of claim 13 wherein the estriol receptor is insolubilized by absorption onto the inner wall of a container.

15. The method of claim 12 wherein the estriol receptor, enzyme composition and the estriol tracer are incubated to permit competition between estriol and estriol tracer for a limited number of estriol receptor binding sites.

16. The method of claim 15 wherein after incubation an antibody capable of binding the receptor is contacted with the receptor to precipitate the receptor.

17. The method of claim 11 wherein the sample is contacted with the estriol receptor at about pH 5.

18. The method of claim 11 wherein the estriol receptor and enzyme composition are mixed together to yield an enzyme-receptor composition which is then contacted with the test sample.

19. The method of claim 18 wherein the pH is about 5.

20. The method of claim 18 wherein the enzyme-receptor composition comprises a dye.

21. The method of claim 11 wherein the receptor is an antibody.

22. The method of claim 11 wherein the enzyme composition comprises a sulfatase and a glucuronidase.

23. In a specific binding assay for the determination of total estriol and estriol conjugates, wherein the improvement comprises, contacting the test sample substantially simultaneously with receptor for estriol and with an enzyme composition suitable for conversion of estriol conjugates to free estriol under conditions suitable for the conversion of the estriol conjugates and for the binding of the estriol by the receptor.

24. The method of claim 23 wherein the receptor is an antibody capable of binding estriol.

25. The method of claim 23 wherein the receptor is a tissue extract capable of binding estriol.

26. The method of claim 23 wherein the receptor is water soluble.

27. The method of claim 23 wherein the enzyme composition comprises a sulfatase and a glucuronidase.

28. A composition for the determination of the total amount of steriod and its conjugates in a test sample consisting essentially of a receptor for the steriod and an amount of enzyme composition suitable for converting the steriod conjugates to the steriod.

29. The composition of claim 28 wherein the receptor is the $Fab_2$ fragment of an antibody.

30. The composition of claim 28 additionally including a tracer.

31. The composition of claim 28 wherein the test sample is human serum or urine.

32. The composition of claim 28 wherein the steroid is aldosterone.

33. The composition of claim 28 wherein the steroid is estriol.

34. The composition of claim 31 additionally including an estriol tracer.

35. The composition of claim 31 having a pH of about 5.

36. The composition of claim 28 wherein the steroid is cortisol.

37. The composition of claim 28 wherein the steroid is testosterone.

38. The composition of claim 28 wherein the steroid is diethylstilbesterol.

39. The composition of claim 28 wherein the enzyme composition includes sulfatase and glucuronidase.

40. The composition of claim 28 wherein the receptor is an antibody.

* * * * *